(12) United States Patent
Castles

(10) Patent No.: US 6,695,825 B2
(45) Date of Patent: Feb. 24, 2004

(54) PORTABLE OSTOMY MANAGEMENT DEVICE

(76) Inventor: Thomas James Castles, 4848 E. Hildreth La., Stockton, CA (US) 95212

( * ) Notice: Subject to any disclaimer, the term of this patent is extended or adjusted under 35 U.S.C. 154(b) by 61 days.

(21) Appl. No.: 09/681,537

(22) Filed: Apr. 25, 2001

(65) Prior Publication Data

US 2002/0161343 A1 Oct. 31, 2002

(51) Int. Cl.[7] ................................................ A61F 5/44
(52) U.S. Cl. ........................................ 604/332; 604/334
(58) Field of Search ................................ 604/332, 333, 604/334, 335, 336, 337, 338, 339, 340, 341, 342, 343, 344, 345

(56) References Cited

U.S. PATENT DOCUMENTS

| | | | | |
|---|---|---|---|---|
| 3,848,173 A | * | 11/1974 | Hase | 320/159 |
| 4,134,404 A | * | 1/1979 | Williams, Jr. | 604/277 |
| 5,330,447 A | * | 7/1994 | Barth | 604/277 |
| 5,454,389 A | * | 10/1995 | Hubbard et al. | 134/104.4 |
| 5,503,633 A | * | 4/1996 | Saunders et al. | 604/332 |
| 6,224,581 B1 | * | 5/2001 | Withers et al. | 604/334 |

* cited by examiner

Primary Examiner—Edward K. Look
Assistant Examiner—John K Fristol, Jr.

(57) ABSTRACT

The "Portable Ostomy Management Device" is a portable, self-contained, powered unit designed to wash and clean the stoma, and interior of drainable ostomy pouches. These pouches are designed to accept the human body waste via the stoma, located on the body of an ostomy patient. This portable system allows an ostomate to position the pouch so it drains into a toilet bowl, permitting the person to wash the pouch interior without removing it from the body or from the barrier section. This portable device allows the ostomate to completely service the ostomy in just a few minutes. The invention includes a carrying case (briefcase, travel bag, soft case, or other containing device), water reservoir, power unit, pump, hoses, control valve, and various other components necessary in controlling power, water pressure and other attributes of this device.

12 Claims, 2 Drawing Sheets

PORTABLE OSTOMY MANAGEMENT DEVICE

BACKGROUND OF THE INVENTION

Thomas J. Castles has been an ostomate for 46 years, having had an "end colostomy" procedure.

According to the International Ostomy Association, and ostomy is best defined as "type of surgery required when a person has lost the normal function of the bladder or bowel due to birth defects, disease, injury or other disorders. Such operations include colostomy, ileostomy and urostomy. The surgery allows for normal bodily wastes to be expelled through a new surgical opening (stoma) on the abdominal wall. Most persons with ostomies must wear special appliances, named "ostomy bags", over the stoma. The ostomy bag retains bodily wastes outside of the body cavity until such time as it can be disposed of properly. An ostomate is a person who has had ostomy surgery. 'Related surgeries' are surgeries of the bowel or urinary system that correct birth defects, illness or injury while preserving continence."

Mr. Castles has done extensive traveling within the United States while vacationing and while serving as a delegate to the American Federation of Musicians. In addition, he has traveled locally as and active performing musician. During these times he has used airliners, cruise ships, trains, motor homes and automobiles, and has been required to maintain his colostomy, which is accomplished by "flushing out" the ostomy bag, using water. This requires Water to be inserted into the bag, and then released back into a portable container, waste basin or toilet. In the past, it has been difficult for such a procedure to be completed when the ostomy patient was away from home, where proper facilities were available, primarily due to the fact that evacuating an ostomy bag can be untidy, unsanitary, and cumbersome without some sort of portable, pressurized water delivery system.

Mr. Castles realized the need for ostomy patients to have a portable service device that allows for efficient, sanitary maintenance of the stoma. The "Portable Ostomy Management Device" provides ostomy patients with a device that is small, portable, and battery powered to provide ostomy maintenance anywhere, at any time. Ostomy patients have no ability to control the normal body function and therefore face extreme stress problems servicing their pouch while at work, visiting, traveling or during other intimate moments in life.

To overcome the difficulties of managing an ostomy when away from equipped facilities, it is necessary to have access to a portable, powered supply of pressurized water that can be used to evacuate and clean out the inside of an ostomy bag while still being worn by the patient. This requires a device that provides a refillable fluid reservoir (1), an on-demand pump (6), a portable power supply or battery (9), a water flow valve (15), and a proprietary, angled pressure wand.

Other devices have been produced to aid in the evacuation and cleaning of ostomy bags, such as those disclosed in the following US Patents:

| U.S. Pat. No. | Inventor(s) | Issue Date |
|---|---|---|
| 4,134,404 | C.B. Williams Jr. | Jan. 16, 1979 |
| 4,642,106 | W. Downey | Feb. 10, 1987 |
| 5,037,408 | J.S. Henry | Aug. 6, 1991 |
| 5,096,503 | S.E. Wellman | Mar. 17, 1992 |
| 5,330,447 | R. Barth | Jul. 19, 1994 |
| 5,454,389 | J.C. Hubbard et al. | Oct. 3, 1995 |
| 5,503,633 | P.K. Saunders et al. | Apr. 2, 1996 |
| 6,224,521 | Withers et al. | May 1, 2001 |

Williams ('404) discloses a colostomy kit, which consists of a small waste receptacle that straps around the waist of the user. The device requires either a plumbing water supply (faucet or spigot), or a water pouch suspended above the user's head, to deliver water to the device. Further, the device is designed for use while patient is sitting on a toilet. This does not provide the user with the ability to use the device when away from plumbing and/or a toilet. Further, the device does not include any sort of angled water delivery nozzle that would minimize the possibility of coming in contact with waste material, or spillage on the user's clothing.

Downey ('106) discloses a device for evacuating the contents of an ostomy bag wherein a pair of elongated members is spaced apart; the ostomy bag is inserted between the elongated members, and then pulled through. As the ostomy bag is pulled between the members, the contents are forced out. This method possibly does not completely clear all materials from the ostomy bag, requiring additional rinsing. This possibly exposes the user to contamination from waste contained within the bag. Further, this device does not provide the user with an angled water delivery nozzle, which is likely to expose the user to contact with unsanitary waste, or spillage on the user's clothing.

Henry ('408) discloses a tool designed to be secured to an ostomy bag so that the bag may be manipulated within a toilet in order to facilitate the evacuation of its contents. This method requires the user to place his or her hands into the toilet with the likely possibility of contamination from both waste within the bag, and from the toilet. Further, this device does not provide the user with an angled water delivery nozzle, which is likely to expose the user to contact with unsanitary waste, or spillage on the user's clothing. Wellman ('503) discloses a device that allows for a hose to be secured to a sink faucet with the purpose of delivering pressurized water inside an ostomy bag in order to flush out waste. This device, however, supplies no means to flush out an ostomy bag when a sink faucet is not available. Further, without an angled water delivery nozzle, the user can possibly make contact with unsanitary waste, or spillage on the user's clothing.

Barth ('447) discloses a device that provides irrigation for an ostomy patient by providing a two-chambered fluid delivery system for flushing out the internal waste channel by inserting a connector to the Stoma. Air-pressurized chamber forces water out of the bag, and into the stoma, using a manual hand-pump. This device is designed for flushing waste from the internal waste channel directly, without the use of an ostomy bag. Further, this device requires substantial effort with two hands in order to complete the flushing task. It provides no means for cleaning the interior of an ostomy bag.

Hubbard ('389) discloses a device for evacuating and capturing waste from an ostomy bag using water delivered with a submersible pump that is installed inside of a fluid reservoir. The device also provides a container for capturing waste. This device requires the user to fill the ostomy bag with fluid, than manually agitate the contents, in order to perform cleaning. Further, without an angled water delivery nozzle and pressurized delivery system, the user is required to agitate the bag, which exposes the risk of making contact with unsanitary waste, or spillage on the user's clothing.

Saunders ('633) discloses a device that provides fixed installation, bedside, or portable use adaptations with the purpose of providing a method for using pressurized water to flush the inside of an ostomy bag. In all three adaptations, the user is required to evacuate waste into a toilet using a specialized component that sits on top of a toilet seat to allow the user to sit and drain the bag contents into a drainage funnel. This device is large, and cumbersome. It is portable (can be moved around within a location), but not transportable (easily taken with a user on trips or vacations). Further, without an angled water delivery nozzle, the user can possibly make contact with unsanitary waste during the bag flushing process, or spillage on the user's clothing.

Withers ('581) provides an ostomy-cleaning device that requires the user to remove the ostomy bag in order to perform said cleaning. The device is designed to be permanently installed near a basin or toilet, and is not transportable or portable. Further, continuously removing and reapplying a new ostomy bag to the stoma can result in irritation to the skin, pain, and discomfort.

Ostomy patients are faced with a dilemma if cleaning is required when the patient is away from home, has no access to bathroom facilities, or is concerned with contaminating the bathroom at the dwelling of another person or at a business. To overcome these objections, the user needs an easy-to-use, pressurized water delivery system that will allow the user to flush an ostomy bag without exposing his or her hands to evacuated waste that will pour out of the bottom of a bottom-opening ostomy bag. To achieve this, water needs to be delivered with an angled pressure wand (16) in order to keep the hands out of the path of evacuated waste.

It is the primary objective of this device to provide a unique delivery component for delivering pressurized water into an ostomy bag to utilize pressure to evacuate waste in a way that prevents users from coming in contact with waste, and keeping waste from spilling or splashing onto the user's clothing by eliminating the need for manual agitation of the bag. This is achieved by providing a water flow valve (15) that has an attached angled pressure wand (16) that has an approximately 30-degree bend. This allows a user to insert the angled pressure wand (16) into the ostomy bag, and then start a pressurized flow of water by activating the water flow valve (15) in order to rinse the bag while the user's hands are out of the evacuation path.

Another objective of this invention is to provide a device that can be used at or away from home by providing a rechargeable battery and/or AC adapter to power an on-demand pump. This is accomplished by providing a commercially available 12-volt battery, AC Charger, DC Charger, and AC Adapter to allow the device to be powered by an internal battery which can be charged with an AC or DC charger.

Another objective of this device is to provide a method for flushing an ostomy bag without having to utilize both hands to manipulate such a device. This is achieved by using the unique angled pressure want (16) and water flow valve (15).

Another objective is to provide a device that can be used with toilets, basins, or any readily available portable container, allowing a user to conduct bag cleaning at any time or place. This device provides the user with such flexibility.

Another objective is to provide a device that is installed in discreet carrying packages such as brief cases, backpacks, purses, and other everyday carrying devices. This is achieved by providing constructing the device with small components that can be discreetly installed in such carrying devices.

BRIEF SUMMARY OF THE INVENTION

The "Portable Ostomy Management Device" is a portable, self-contained, ostomy bag cleaning device designed to deliver pressurized water into an into an ostomy bag (20), while being worn by an ostomy patient, in order to loosen and complete the evacuation of the waste therein, into a disposal container of the user's choosing—including home toilets, portable toilets, portable containers, or other containment vessels. This portable ostomy management device includes a fluid reservoir (1), fill stem (2), and fill cap (3) for storing clean water used for washing out the ostomy bag (20). An on-demand pump (6) that draws water from the fluid reservoir (1) supply stem (4) through a short segment of flexible hose (5) whenever the water flow valve (15) is engaged by the user. The pump (6) delivers water into a long flexible hose (7) that carries the water from the pump (6) to the water flow valve (15). When engaged, the water flow valve (15) delivers water into the pressure wand (16), which forces the water out of the device through a pressure nozzle (17). The pressurized water then loosens any trapped waste within the ostomy bag (20), and allows it to drain out of the bottom of the ostomy bag (20) and into a disposal container, toilet, or other containment vessel. An override switch (8) is provided in case the pump (6) built-in "on-demand" capability fails to stop the pump's (6) operations. A re-chargeable, portable battery pack (9) is provided to power the pump (6). A battery-charging unit (10) is provided to stabilize DC current provided to charge the battery. An AC to DC charging component (11), terminated with an acceptable connector plug (13), can be used to plug into the battery charging unit (10) from an AC power source, to perform battery charging. A DC charging component for automobile cigarette lighter plugs (12), terminated with an acceptable connector plug (13), can be used to plug into the battery charging unit (10) from a DC power source, to perform battery charging. A discreet, rigid carrying case structure (18) such as a briefcase, or a non-rigid carrying case such as a nylon backpack or carry bag, are used to house all of the components of the portable ostomy management device.

BRIEF DESCRIPTION OF THE SEVERAL VIEWS OF THE DRAWING

FIG. 1.2: This is a diagram of the water flow valve (15), with the pressure wand (16) and pressure nozzle (17) inserted into an ostomy bag, with cleaning being conducted while a patient is wearing the ostomy bag (20).

DETAILED DESCRIPTION OF THE INVENTION

Figure 1:
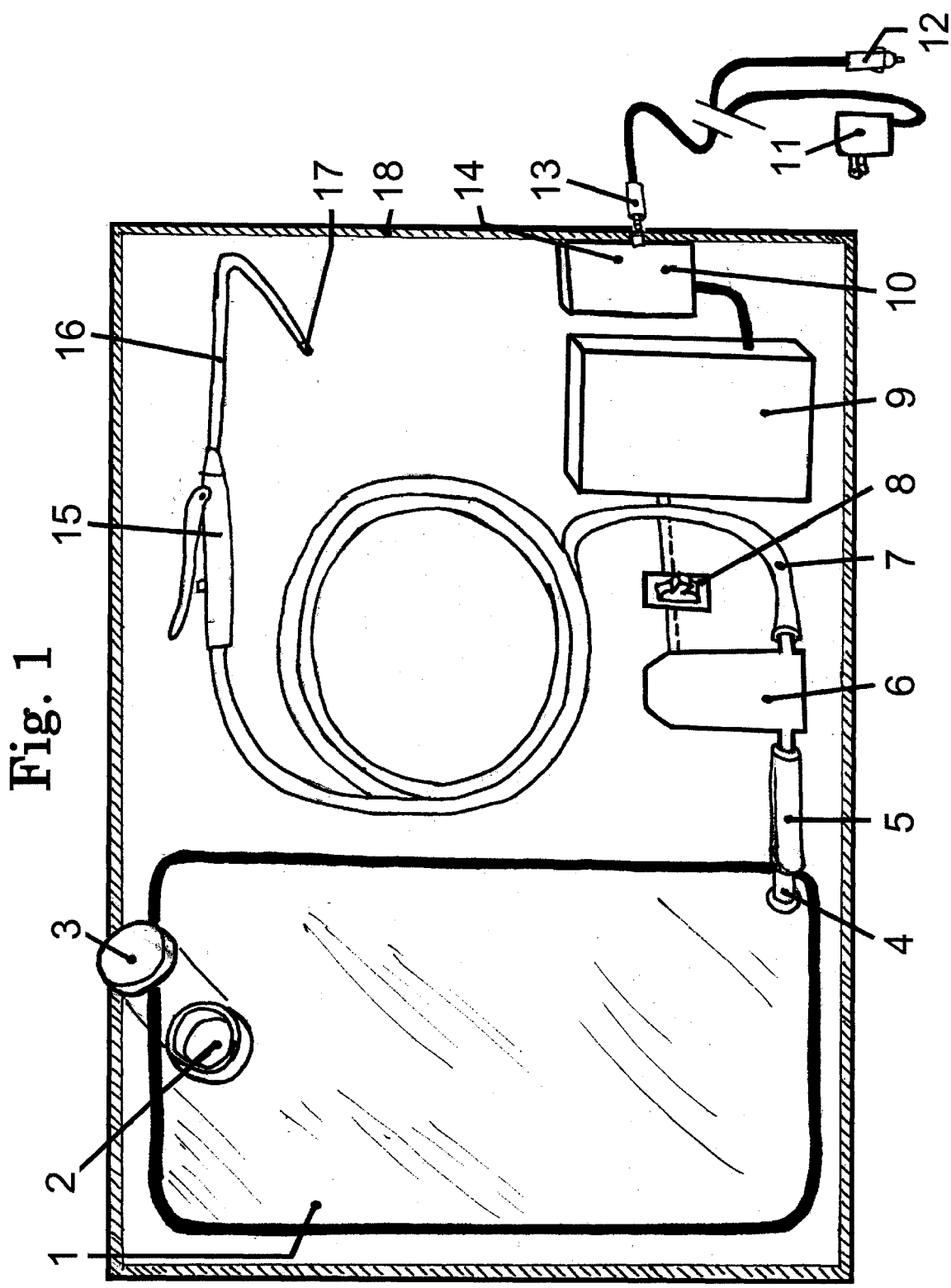
FIG. 1.1: This diagram illustrates the major components of the device.
Figure 2:
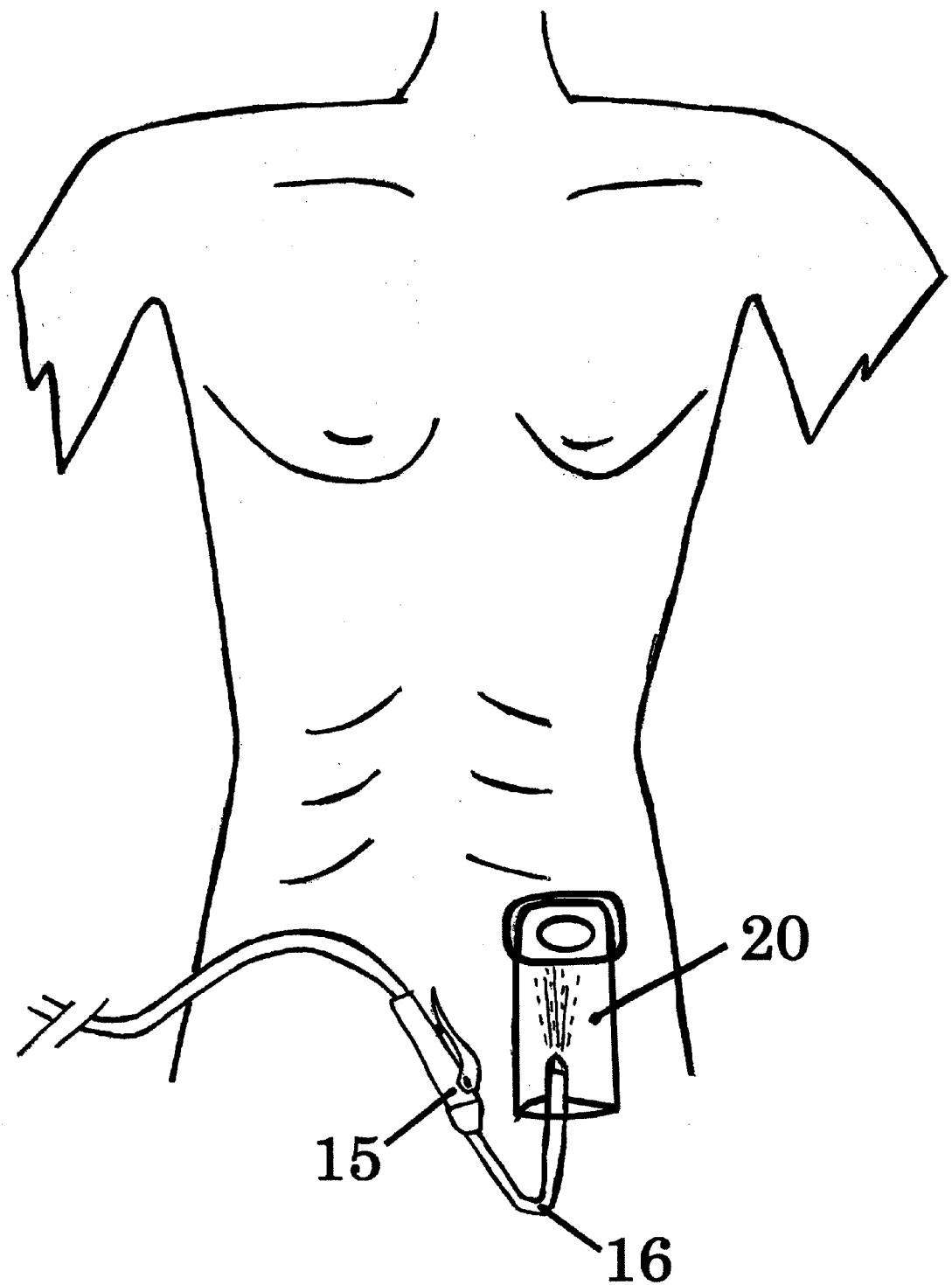

This device consists of five (5) major sub-assemblies. These sub-assemblies, collectively, constitute the "Portable Ostomy Management Device". In detail, the sub-assemblies consist of:

Discreet Carrying Case Assembly

This device can be installed in almost any type of portable carrying container or case, including but not limited to, a rigid Briefcase (18), non-rigid Soft Carrying Case, non-rigid Purse, non-rigid Backpack, non-rigid Travel Bag, rigid Suitcase, non-rigid Camera Bag, or any other transportation apparatus.

Power Unit Assembly

The power unit consists of a 12-volt DC battery pack (9). The power unit also has a built-in fuse assembly and an override switch (off and on) on the positive lead wire between the battery and water pump terminal. This switch provides shutoff in the event that the water supply is completely exhausted, or the "on-demand" capability of the pump (6) fails to shut off pump (6) operations. The power unit assembly also contains a battery charging circuit (10), input plug (13), AC to DC charging adapter (11), and/or a DC charging plug (12) for re-charging the battery using DC or AC power sources.

Fluid Reservoir Component

The water reservoir consists of a container for holding water used during the operation of the device. The reservoir can be a non-rigid water flask, non-rigid plastic water bag, rigid plastic container, or any other water-containing unit. The type of fluid reservoir used will depend upon the carrying container selected to house the device.

Pump Assembly

The pump assembly consists of a 1 Gallon Per Minute, DC powered, on-demand pump unit (6) that has a built-in pneumatic-switch that automatically turns off the pump when flow of water ceases due to the user disengaging the water flow valve (15). As a result, the water pressure in the pumping unit reaches 30 pounds per square inch, causing the pump (6) "on-demand" feature to turn off the pump (6) motor. Attached to the pump are two water delivery hoses. The first is a short flexible hose (5) that delivers water from the fluid reservoir (1) to the pump (6). The second is a long flexible hose (7) that delivers water from the pump (6) to the water flow valve (15).

Water Flow Control Assembly

The water flow assembly consists of a water flow valve (15) that, when activated, allows water to flow into a uniquely angled pressure wand (16) and out of a pressure nozzle (17) for purposes of using pressurized water to flush out waste from an ostomy bag (20). The water flow valve (15) features an manually activated on/off controller mechanism that, when depressed, begins water flow. Further, by depressing the mechanism, the pressure is relieved in the hose between the flow valve and the pump (6), thus signaling the pump's (6) pneumatic control to begin on-demand service by closing the electrical circuit in the pump, which results in the pump being engaged. Attached to the water flow valve is a pressure wand (16) that is terminated with a pressure nozzle (17). The pressure wand (16) is bent at an angle that easily allows insertion into the bottom of an open ostomy bag (6), without discomfort to the user, and in such a manner as to protect the user from the waste stream exiting the ostomy bag.

Making the Device

The prototype device was manufactured using a standard business briefcase, a sealed DC battery, a flexible plastic water flask, hose, a Flojet brand water pump and a commercially available water control valve.

A mounting board was permanently installed into the bottom of the briefcase.

The power unit, slide switch, water reservoir and pump components were installed onto the mounting board in such a fashion as to ensure they will not become un-installed during normal use and transport of the device, yet allowing the components to be removed should they require service or replacement.

The negative (−) battery terminal was then wired to the negative (−) input post of the battery charging plug, and then wired in series to the negative (−) power post on the pump.

The positive (+) battery terminal was then wired to the input post of the fuse. The output post of the fuse was then wired to the input post of the battery-charging plug, and then wired in series to the positive (+) input post on the slide switch. The output post on the slide switch was then wired to the positive (+) power post on the pump, thus completing the pump wiring installation.

Installation of the water input hose required a length of clear hose that was installed on the hose connector of the water flask; the hose connector having been pre-manufactured into the filler cap of the flask. The opposite end of the hose was connected to the input port of the pump and secured with a metal ring clamp, thus completing the installation of the water input hose.

Installation of the water output hose required a length of clear hose that was installed on the output port of the pump and secured using a metal ring clamp. The opposite end of the hose was installed onto a brass hose connector located at the base of the water control valve, and secured with a metal ring clamp, thus completing the installation of the water output hose.

Configuration of the water control valve was accomplished by installing a rubber coupling tube onto the brass spigot located on the end of the valve component. In the opposite end of the coupling tube, a clear plastic extension was inserted, thus completing the configuration of the water control valve.

Using the Device

This device is portable, and is designed to be used anywhere, including out in the "wild" while on hunting, fishing, hiking or camping trips. The typical user follows this sequence of events to use the device:

Step 1: Charging The Battery

The power unit component consists of an AC Charging unit that provides the ability to charge the internal battery pack using a standard AC or DC charging unit. Before using the device, the battery must be charged. To accomplish this, the user simply plugs the Charging unit into any AC or DC Power outlet, and the opposite end plug into the charging jack on the side of the Portable Ostomy Management Device.

Step 2: Filling The Fluid Reservoir

Before the unit can be used, the use must fill the water reservoir by simply opening the water filler cap and filling the reservoir with tap water.

Step 3: Turning On The Power

In order to turn on power to the pump unit, the override slide switch (on/off) of the power unit must be set to the "on" position.

Step 4: Operation

Once steps 1 through 3 are completed, the device is ready to be used.

Typically, a user first opens the clip on the bottom of an ostomy bag (20), positions it over or inside of a toilet or other waste disposal container, and then allows gravity to evacuate the majority of the contents of the ostomy bag (20) into the toilet or other waste disposal container. Once this is completed, the ostomy bag (20) must be cleaned of any remaining waste that may not have been evacuated by simple gravity. In this instance, it is necessary to use pressurized water to rinse out the ostomy bag (20) while it is still positioned in the disposal container. This requires a water flow control assembly, which consists of a water flow valve (15) that has a bent pressure wand (16) assembly, and a pressure nozzle (17) that can be inserted into the bottom of the ostomy bag (20) without undue discomfort to the user, in order to deliver a stream of pressurized water for cleaning.

Once the user is ready to begin cleaning the ostomy bag (20), he/she simply begins the flow of water by activating the water control valve. This causes a drop in hose pressure between the valve and the output port of the pump, which activates the pump unit. Pressurized water begins to flow, which is used to clean the interior of the ostomy bag (20).

To stop the flow of water, the user simply releases the water control valve, which builds pressure in the hose between the valve and the output port of the pump unit. The pump's on-demand feature senses this and shuts the pump unit off.

Once water is flowing, the user can wash the stoma area and flush out the waste pouch while sitting on, next to, or kneeling besides a toilet bowl. The metered flow from the control valve should not be entered into the stoma opening. The user should apply a pattern of short bursts of water to conserve the reservoir supply.

When the cleaning process is completed, turn off switch, open control valve to drain hose, and then refill the water supply.

Distinguishing Characteristics

Major distinguishing characteristics include:

A unique angled pressure wand (16) allows a user to flush the contents of an ostomy bag without exposing hands or clothing to spillage and/or contamination.

Delivering pressurized water via a DC battery powered (9) on-demand pump (6), which eliminates the need to agitate the ostomy bag (20), as is required by the device patented by Hubbard et al. (U.S. Pat. No. 5,454,389).

The use of an on-demand pump (6) eliminates the need for a manual, primary on/off switch to activate/deactivate the water flow. Instead, pressure within the delivery hose (7) is sensed by the pump. An increase in pressure caused by disengaging the water flow valve (15) automatically turns the pump off. A release of pressure caused by the engaging the water flow valve (16) automatically turns the pump on.

A discreet carrying case (briefcase, backpack, soft pack) makes the device easy to carry and indistinguishable from other commonly used carrying devices.

On-demand pumping and the water flow valve eliminate the need for the device to be worn during operation (as required by Hubbard U.S. Pat. No. 5,454,389). It further frees up the user's hands by not requiring the second hand to be used to turn the device on and off.

Use of a readily available portable waste container is optional, which eliminates the need for later disposal and possible exposure to waste in the event the container is breached—should the user choose such an option.

Use of a simple plug-in battery charger makes it fast and easy to re-charge the self-contained battery pack using either AC or DC power sources. The size and amperage of the battery pack allows the portable ostomy management device to be used many times on a single charge.

What is claimed is:

1. A portable ostomy management device that provides a unique method for cleaning the interior of an ostomy bag while at home, or away from home that is comprised of
   a. a fluid reservoir
   b. an on-demand DC powered pump
   c. a fluid delivery hose and a water flow valve
   d. a angled pressure wand and a pressure nozzle
   e. a pump emergency shutoff switch
   f. a rechargeable battery pack and a charger
   g. a discreet carrying case or container.

2. The device of claim 1 wherein said fluid reservoir is provided with a removable closure device for opening and closing said reservoir to perform refilling.

3. The device of claim 1 wherein said fluid reservoir has an outlet and flexible hose for transporting fluid from said reservoir to said input terminal on said on-demand pump.

4. The device of claim 1 wherein said on-demand pump includes an outlet terminal onto which is attached said flexible hose for directing flow of said fluids to said water flow valve.

5. The device of claim 1 wherein said angled pressure wand is attached to said water flow valve for the purpose of directing flow of said water through said pressure nozzle.

6. The device of claim 1 wherein said pump is provided with direct DC current source which passes electrical current through said override switch that is provided for the purpose of emergency shutoff of said on-demand pump.

7. The device of claim 1 wherein said charging unit restores electrical charge to said battery utilizing said AC or DC charging components.

8. The device of claim 1 wherein said reservoir, said pump, said hose, said angled pressure wand, and said electrical components are contained within a discreet and portable carrying case.

9. The device of claim 1 wherein said angled pressure wand provides for delivery of pressurized water into the interior of an ostomy bag, and whereas said angle helps reduce the chances of contact with waste during flushing operations by eliminating the need for manual agitation of the bag and contents.

10. The device of claim 1 wherein said water flow valve provides engagement/disengagement of said on-demand water pump by sensing the presence, or lack of pressure at said outlet terminal of said pump.

11. The device of claim 1 wherein said device is contained within said portable and discreet carrying case.

12. A portable device for cleaning an ostomy bag, said device comprising:
   a. a fluid reservoir for retaining water a reservoir being provided with a fill stem and a cap for opening, closing, and refilling fluids within said reservoir
   b. an on-demand pump for transporting said water from said reservoir into said ostomy bag
   c. a flexible hose for delivering water from an output terminal on said pump to a water flow valve
   d. said water flow valve for initiating the flow of water through said pump, using the pressure-sensing capability of said on-demand pump
   e. a angled pressure wand for transporting said water from said water flow valve through said pressure nozzle for the purpose of creating a pressurized stream of water used to loosen waste from the inside of said ostomy bag.

* * * * *